United States Patent
Maj

(10) Patent No.: US 6,667,329 B1
(45) Date of Patent: *Dec. 23, 2003

(54) AGENTS WITH ANTIDEPRESSANT ACTION, CONTAINING PRAMIPEXOL AND SECOND ANTIDEPRESSANT

(75) Inventor: Jerzy Maj, Cracow (PL)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/743,190

(22) Filed: Jul. 6, 2000

Related U.S. Application Data

(63) Continuation of application No. PCT/EP98/04691, filed on Jul. 27, 1998.

(51) Int. Cl.⁷ ..................... A61K 31/425; A61K 31/136
(52) U.S. Cl. ......................................... 514/367; 514/647
(58) Field of Search ................................. 514/367, 647

(56) References Cited

U.S. PATENT DOCUMENTS

| | | | |
|---|---|---|---|
| 6,117,855 A | * | 9/2000 | Carlson et al. .......... 514/236.2 |
| 6,191,153 B1 | * | 2/2001 | Hammer et al. ............ 514/367 |
| 6,255,329 B1 | * | 7/2001 | Maj ........................... 514/367 |

OTHER PUBLICATIONS

Maj et al. Antidepressant effects of pramipexole, a novel dopamine receptor agonist, 1997, Journal of Neural Transmission, vol. 104, pp. 525–533.*

* cited by examiner

*Primary Examiner*—Shep K. Rose
*Assistant Examiner*—Donna Jagoe
(74) *Attorney, Agent, or Firm*—Robert P. Raymond; Timothy X. Witkowski; Anthony P. Bottino

(57) ABSTRACT

The present invention relates to the use of 2-amino-4,5,6,7-tetrahydro-6-propylamino-benzothiazole (pramipexole), the (+)- or (−)-enantiomer thereof or one of the pharmacologically acceptable salts thereof in conjunction with another antidepressant for the improved treatment of depression and depressive states.

18 Claims, No Drawings

AGENTS WITH ANTIDEPRESSANT ACTION, CONTAINING PRAMIPEXOL AND SECOND ANTIDEPRESSANT

RELATED APPLICATIONS

This application is a continuation of International Application PCT/EP98/04691, filed on Jul. 27, 1998. Benefit of the filing date of the prior International Application is hereby claimed, pursuant to 35 U.S. C. §§365(c) and 120.

FIELD OF THE INVENTION

The present invention relates to an agent with an antidepressant activity containing 2-amino-4,5,6,7-tetrahydro-6-propylamino-benzothiazole or the (+) or (−)enantiomer thereof, the pharmacologically acceptable acid addition salts thereof and a conventional antidepressant.

PRIOR ART

Pramipexole-2-amino-6-n-propylamino4,5,6,7-tetrahydrobenzo-thiazole-dihydrochloride—is a dopamine-$D_3/D_2$ agonist, the synthesis of which is described in European Patent 186 087. Pramipexole is known primarily for treating schizophrenia and particularly for the treatment of Parkinson's disease. German Patent Application DE 38 43 227 discloses that pramipexole lowers the prolactin serum level, and it is also known from German Patent Application DE 39 33 738 to use pramipexole to lower high TSH levels. Its transdermal administration is disclosed in U.S. Pat. No. 5,112,842, and WO Patent Application PCT/EP93/03389 describes the use of pramipexole as an antidepressant.

Details of the preparation of the title compound can be found in EPO/86 087A1, and reference is hereby made specifically to the literature cited therein.

DESCRIPTION OF THE INVENTION

It has now been found that, surprisingly, pramipexole combined with another antidepressant has a significantly greater antidepressant activity than either of the two individual components taken alone. The fact that the combination of active substances takes effect immediately should be particularly emphasised.

The improvement in the effect of pramipexole by the simultaneous administration of another antidepressant was discovered in tests on rats using the so-called "forced swimming test". Details of this test method can be found, for example, in Willner, Psychopharmacology 83, 1–16 (1984) or Borsini and Meli, Psychopharmacology 94, 147–160 (1988).

The test can be carried out as follows for each of the combinations of active substances tested. The animals were divided up into different groups and each group was given either a saline solution, a therapeutically effective amount of pramipexole, a therapeutic amount of a second antidepressant other than pramipexole or a combined dose of pramipexole and the other antidepressant in the same therapeutic amount as the animals that received only one of the two active substances.

A selection of the results of the tests is shown in Table 1:

TABLE 1

| Combination of active substances | Groups (active substance in mg/kg) | Immobility time(s) |
|---|---|---|
| Pramipexole + imipramine | Common salt | 207.4 ± 10.2 |
| | Pramipexole | 129.4 ± 8.1 |
| | Imipramine | 147.3 ± 10.5 |
| | Pramipexole + imipramine | 40.8 ± 9.7 |
| Pramipexole + amitriptyline | Common salt | 231.3 ± 8.2 |
| | Pramipexole | 164.3 ± 9.8 |
| | Amitriptyline | 174.6 ± 9.2 |
| | Pramipexole + amitriptyline | 55.6 ± 8.7 |
| Pramipexole + citalopram | Common salt* | 231.3 ± 8.2 |
| | Pramipexole* | 164.3 ± 9.8 |
| | Citalopram | 233.5 ± 9.8 |
| | Pramipexole + citalopram | 82.1 ± 11.2 |
| Pramipexole + fluoxetin | Common salt | 221.4 ± 4.9 |
| | Pramipexole | 131.0 ± 10.0 |
| | Fluoxetin | 236.9 ± 7.4 |
| | Pramipexole + fluoxetin | 80.2 ± 10.7 |

*Group is identical to group from the series Pramipexole plus amitriptyline

The results described above demonstrate the clearly improved effect of the combined administration of pramipexole and another antidepressant compared with the administration of the individual substances.

Other embodiments relate to the combined administration of pramipexole with one of the following antidepressants:

| | | |
|---|---|---|
| alprazolam | fluoxetin | opipramol |
| amitriptyline | fluvoxamine | paroxetine |
| amitriptyline oxide | imipramine | sertraline |
| chlordiazepoxide | lofepramine | sulpiride |
| citalopram | maprotiline | tranylcypromine |
| clomipramine | mianserin | trazodone |
| chinpirol | mirtazapine | trimipramine |
| dibenzepin | moclobemide | tryptophan |
| doxepin | Nefazodone | venlafaxine or |
| | Nortriptyline | viloxazine |

The combination of pramipexole and another antidepressant may be formulated analogously to conventional galenic preparations, generally together with a pharmaceutical carrier. In other words an effective dose of the individual components and optionally a pharmaceutical carrier are formulated as plain or coated tablets, capsules, lozenges, powders, solutions, suspensions, emulsions, syrups, suppositories etc. For pramipexole the pharmaceutically effective dose per patient is between 0.01 and 10 mg, preferably between 0.08 and 5 mg.

The therapeutically effective doses of the second antidepressant in the combination are given in the Table which follows.

| | |
|---|---|
| (25–100 mg) | alprazolam, |
| (10–50 mg) | Amitriptyline, |
| (30–120 mg) | Amitriptyline oxide |
| (5 mg) | chlordiazepoxide, |
| (20–40 mg) | Citalopram, |
| (10–25 mg) | Clomipramine, |
| (1–5 mg) | chinpirol, |
| (10–250 mg) | Dibenzepin, |
| (5–50 mg) | doxepin, |
| (10–30 mg) | Fluoxetin, |
| (50–100 mg) | fluvoxamine, |

-continued

| | |
|---|---|
| (10–25 mg) | Imipramine, |
| (35–75 mg) | lofepramine, |
| (10–75 mg) | maprotiline, |
| (10–30 mg) | mianserin, |
| (30 mg) | Mirtazapine, |
| (150–300 mg) | Moclobemide, |
| (100–300 mg) | Nefazodone, |
| (10–25 mg) | Nortriptyline, |
| (50 mg) | Opipramol, |
| (20 mg) | Paroxetin, |
| (50 mg) | Sertraline, |
| (50–200 mg) | Sulpiride, |
| (10 mg) | Tranylcypromine, |
| (25–100 mg) | Trazodone, |
| (25–250 mg) | Trimipramine, |
| (500 mg–2.5 g) | Tryptophan, |
| (30–75 mg) | Venlafaxine or |
| (100 mg) | Viloxazine. |

In the combination according to the invention the recommended dose may in individual cases be below the single dose previously recommended for the monopreparation.

The term combination for the purposes of the invention refers to an active substance combination of the two active substances in a formulation and also as a combination in the sense of individual formulations of the active substances administered at specified intervals from one another in a therapeutic treatment. Orally administered pharmaceutical formulations for pramipexole are known from the prior art and are obtainable under the brand name Sifrol.

The individual active substances may also be packaged in kit form as a combined pack of the individual drugs, as well as separately.

What is claimed is:

1. A pharmaceutical composition for treating depression, comprising:
    (a) 2-amino-4,5,6,7-tetrahydro-6-propylaminobenzothiazole, one of the enantiomers thereof, or one of the acid addition salts thereof; and
    (b) second antidepressant.

2. The pharmaceutical composition according to claim 1, comprising the (+)-enantiomer of 2-amino-4,5,6,7-tetrahydro-6-propylaminobenzothiazole or one of the acid addition salts thereof.

3. The pharmaceutical composition according to claim 1, comprising the (−)-enantiomer of 2-amino-4,5,6,7-tetrahydro-6-propylaminobenzothiazole or one of the acid addition salts thereof.

4. The pharmaceutical composition according to one of claims 1 to 3, comprising 2-amino-4,5,6,7-tetrahydro-6-propylaminobenzothiazole dihydrochloride.

5. The pharmaceutical composition according to one of claims 1 to 3, comprising 2-amino-4,5,6,7-tetrahydro-6-propylaminobenzothiazole dihydrochloride monohydrate.

6. The pharmaceutical composition according to one of claims 1 to 3, wherein the second antidepressant is selected from the group consisting of: alprazolam, amitriptyline, amitriptyline oxide, chlordiazepoxide, citalopram, clomipramine, chinpirol, dibenzepin, doxepin, fluoxetine, fluvoxamine, imipramine, lofepramine, maprotiline, mianserin, mirtazepine, moclobemide, nefazodone, nortriptyline, opipramol, paroxetine, sertraline, sulpiride, tranylcypromine, trazodone, trimipramine, tryptophan, venlafakine, and viloxazine.

7. The pharmaceutical composition according to one of claims 1 to 3, wherein the second antidepressant is selected from the group consisting of: amitriptyline, citalopram, chinpirol, and fluoxetine.

8. The pharmaceutical composition according to one of claims 1 to 3, wherein the second antidepressant is selected from the group consisting of: amitriptyline, citalopram, and fluoxetine.

9. The pharmaceutical composition according to one of claims 1 to 3, wherein the pharmaceutical composition comprises 0.05 mg to 10 mg of 2-amino-4,5,6,7-tetrahydro-6-propylaminobenzothiazole, one of the enantiomers, or one of the acid addition salts thereof, pramipexole or pramipexole-dihydrochloride-monohydrate.

10. The pharmaceutical composition according to claim 1, wherein the pharmaceutical composition comprises 0.088 mg to 1.5 mg of 2-amino-4,5,6,7-tetrahydro-6-propylaminobenzothiazole, one of the enantiomers or one of the acid addition salts thereof.

11. The pharmaceutical composition according to claim 1, wherein the pharmaceutical composition comprises 10 mg to 50 mg of amitriptyline, 20 mg to 40 mg of citalopram, 10 mg to 25 mg of chinpirol, or 10 mg to 30 mg of fluoxetine.

12. The pharmaceutical composition according to claim 1, wherein the second antidepressant is sertraline.

13. The pharmaceutical composition according to claim 12, wherein the pharmaceutical composition comprises between 0.088 mg and 1.1 mg of pramipexole or between 0.125 mg and 1.5 mg of pramipexole dihydrochloride monohydrate.

14. The pharmaceutical composition according one of claims 12 and 13, wherein the pharmaceutical composition comprises between 25 mg and 200 mg of sertraline.

15. The pharmaceutical composition according to claim 12, wherein the pharmaceutical composition comprises 50 mg of sertraline.

16. A method of treating depression or depressive states in a host in need of such treatment comprising administering to the host a pharmaceutical composition according to one of claims 1 to 3.

17. A method of treating depression or depressive states in a host in need of such treatment, the method comprising administering to the host the pharmaceutical composition according to claim 1.

18. A method of treating depression or depressive states in a host in need of such treatment, the method comprising administering successively over time to the host compounds (a) and (b):
    (a) 2-amino-4,5,6,7-tetrahydro-6-propylaminobenzothiazole, one of the enantiomers thereof, or one of the acid addition salts thereof; and
    (b) a second antidepressant.

* * * * *